United States Patent
Rodrigues et al.

(10) Patent No.: US 7,063,895 B2
(45) Date of Patent: Jun. 20, 2006

(54) HYDROPHOBICALLY MODIFIED SOLUTION POLYMERS AND THEIR USE IN SURFACE PROTECTING FORMULATIONS

(75) Inventors: Klein Rodrigues, Signal Mountain, TN (US); Michael Eknoian, Warren, NJ (US); Martin Crossman, Hixson, TN (US)

(73) Assignee: National Starch and Chemical Investment Holding Corporation, New Castle, DE (US)

( * ) Notice: Subject to any disclaimer, the term of this patent is extended or adjusted under 35 U.S.C. 154(b) by 0 days.

(21) Appl. No.: 09/920,498

(22) Filed: Aug. 1, 2001

(65) Prior Publication Data

US 2003/0072950 A1 Apr. 17, 2003

(51) Int. Cl.
*B32B 27/30* (2006.01)

(52) U.S. Cl. ............... 428/461; 428/473; 428/500; 428/510; 428/522; 427/384; 523/105; 526/328; 526/328.5

(58) Field of Classification Search ............ 428/461, 428/500, 473, 510, 522, 411.1; 427/384; 526/328, 328.5; 523/105, 535
See application file for complete search history.

(56) References Cited

U.S. PATENT DOCUMENTS

| | | | | |
|---|---|---|---|---|
| 2,536,050 A | | 1/1951 | Fluck, Jr. ............ | 442/107 |
| 4,119,600 A | | 10/1978 | Bakule et al. ............ | 260/29.6 |
| 4,568,737 A | * | 2/1986 | Tomalia et al. ............ | 528/332 |
| 4,596,668 A | | 6/1986 | Berbeco ............ | 252/500 |
| 4,623,689 A | | 11/1986 | Shintani et al. ............ | 524/457 |
| 4,914,170 A | | 4/1990 | Chang et al. ............ | 526/240 |
| 4,923,514 A | | 5/1990 | Brown ............ | 106/11 |
| 4,960,463 A | | 10/1990 | Brown ............ | 106/11 |
| 5,227,421 A | | 7/1993 | Kageyama et al. ............ | 524/449 |
| 5,312,883 A | | 5/1994 | Komatsu et al. ............ | 526/318.44 |
| 5,324,445 A | | 6/1994 | Langley et al. ............ | 510/321 |
| 5,364,737 A | * | 11/1994 | Barr ............ | 430/281.1 |
| 5,492,599 A | | 2/1996 | Olson et al. ............ | 162/137 |
| 5,527,853 A | | 6/1996 | Landy et al. ............ | 524/521 |
| 5,770,548 A | | 6/1998 | Leskowicz et al. ............ | 510/181 |
| 6,013,721 A | | 1/2000 | Schall et al. ............ | 524/555 |
| 6,040,409 A | | 3/2000 | Lau et al. ............ | 526/328 |
| 6,150,468 A | * | 11/2000 | Schoenberg et al. ............ | 525/222 |
| 6,200,640 B1 | * | 3/2001 | Kneip et al. ............ | 280/728.2 |
| 6,303,190 B1 | | 10/2001 | Linert et al. ............ | 427/387 |
| 6,337,359 B1 | * | 1/2002 | Diehl et al. ............ | 523/201 |
| 6,420,479 B1 | * | 7/2002 | Phan et al. ............ | 524/800 |
| 6,488,764 B1 | * | 12/2002 | Westerman ............ | 523/201 |

FOREIGN PATENT DOCUMENTS

| | | |
|---|---|---|
| JP | 4320467 | 11/1992 |
| JP | 4335070 | 11/1992 |
| JP | 4335071 | 11/1992 |

* cited by examiner

*Primary Examiner*—D. Lawrence Tarazano
(74) *Attorney, Agent, or Firm*—David P. LeCroy

(57) ABSTRACT

The present invention is directed to an aqueous polymer composition comprising a copolymer and water, the copolymer containing at least one hydrophilic base or acid-neutralizable monomer and at least one hydrophobic ethylenically unsaturated monomer. A film formed from the contains essentially no crosslinking. The polymer composition is formed by polymerizing the hydrophilic monomer and hydrophobic monomer in a non-aqueous solvent; forming an aqueous polymer dispersion from the non-aqueous polymer solution, and adding a base or acid to form an aqueous polymer composition.

20 Claims, 2 Drawing Sheets

THOMPSON'S

EXAMPLE 4

HYDROPHOBICALLY MODIFIED SOLUTION POLYMERS AND THEIR USE IN SURFACE PROTECTING FORMULATIONS

The present invention relates to a surface-protecting formulation containing an aqueous polymer composition capable of forming a film, the film being essentially free of crosslinking. In particular the formulation imparts hydrophobic properties to a material, providing water-repellency to materials such as metal, glass, ceramics, leather, wood, construction materials, and fabric, as well as providing fabric sizing, anti-pilling and color protection properties to fabrics and textiles. The environmentally friendly formulation can be used as a replacement for silicones and polyethylene-based coatings currently employed in these applications.

BACKGROUND OF THE INVENTION

Polymer coatings are used in many applications to impart durability and water resistance. Polymer coatings can be produced from a clear solution of a polymer in a non-aqueous solvent, such as lacquers. For ecological reasons, however, aqueous polymer solutions or emulsions are preferred over those based on organic solvents. Water resistant coatings containing silicones and polyethylene emulsions are currently used for this purpose.

U.S. Pat. No. 5,770,548 discloses hard surface cleaners containing silicates and hydrophobic acrylic polymer.

U.S. Pat. Nos. 4,923,514; 4,960,463; and 6,040,409 disclose aqueous floor polish compositions useful as wax replacements. The compositions contain polymers with high acid levels, which are capable of being stripped or dissolved by alkali solutions. These polymers also require a $C_{16-40}$ monomer.

U.S. patent application Ser. No. 09/690387 describes aqueous polymer compositions containing a copolymer having at least one hydrophilic base-neutralizable monomer and at least one hydrophobic ethylenically unsaturated monomer, wherein said polymer composition is clear, wherein a film formed from said polymer composition is insoluble in water once formed, and wherein said film contains essentially no crosslinking. No compositions are disclosed using said copolymer in a coating or textile formulation.

Surprisingly it has been found that formulations formed with an aqueous polymer composition which forms a film without the existence of crosslinking, provide many useful properties to substrates coated with said formulation. The ability to easily and quickly form a film from a water-borne polymer, then having said film being water resistant, provides an economical and ecologically friendly means to provide water, wear and weather resistance to a variety of substrates including wood, metal, glass, ceramics, leather, carpets, plastic, upholstery, skin, hair, paper, non-wovens, and fabric. Formulations of the present invention also serve as a sizing and anti-pilling agent for fabrics and textiles. An advantage of the present invention over current technology is that no external energy is required to facilitate a crosslinking reaction

SUMMARY OF THE INVENTION

The present invention is directed to a composition comprising an aqueous polymer composition comprising a copolymer and water, wherein said copolymer comprises at least one hydrophilic monomer and at least one hydrophobic ethylenically unsaturated monomer, wherein a film formed from said polymer composition contains essentially no crosslinking.

The invention is also directed to a formulation comprising an aqueous polymer composition comprising a) a copolymer, wherein said copolymer comprises at least one hydrophilic monomer and at least one hydrophobic ethylenically unsaturated monomer, wherein said composition is a solution or a dispersion, and wherein a film formed from said polymer composition contains essentially no crosslinking;

b) water; and c) a component selected from the group consisting fillers, anti-fungal and anti-microbial agents, pigments, perfumes, surfactants, builders, co-builders, antioxidants, enzymes, brighteners, dispersants, antifoaming agents, preservatives, water-softening agents, sunscreen agents, and mixtures thereof.

The invention is also directed to a coated substrate comprising a substrate having on at least one surface a film formed from an aqueous polymer composition comprising a copolymer comprising at least one hydrophilic monomer and at least one hydrophobic ethylenically unsaturated monomer, wherein a film formed from said polymer composition contains essentially no crosslinking.

A further embodiment of the invention is a process for imparting water proofing, wear resistance, weather resistance, and durability to a substrate, by applying the coating formulation of the present invention.

DETAILED DESCRIPTION OF THE INVENTION

Figure 1:
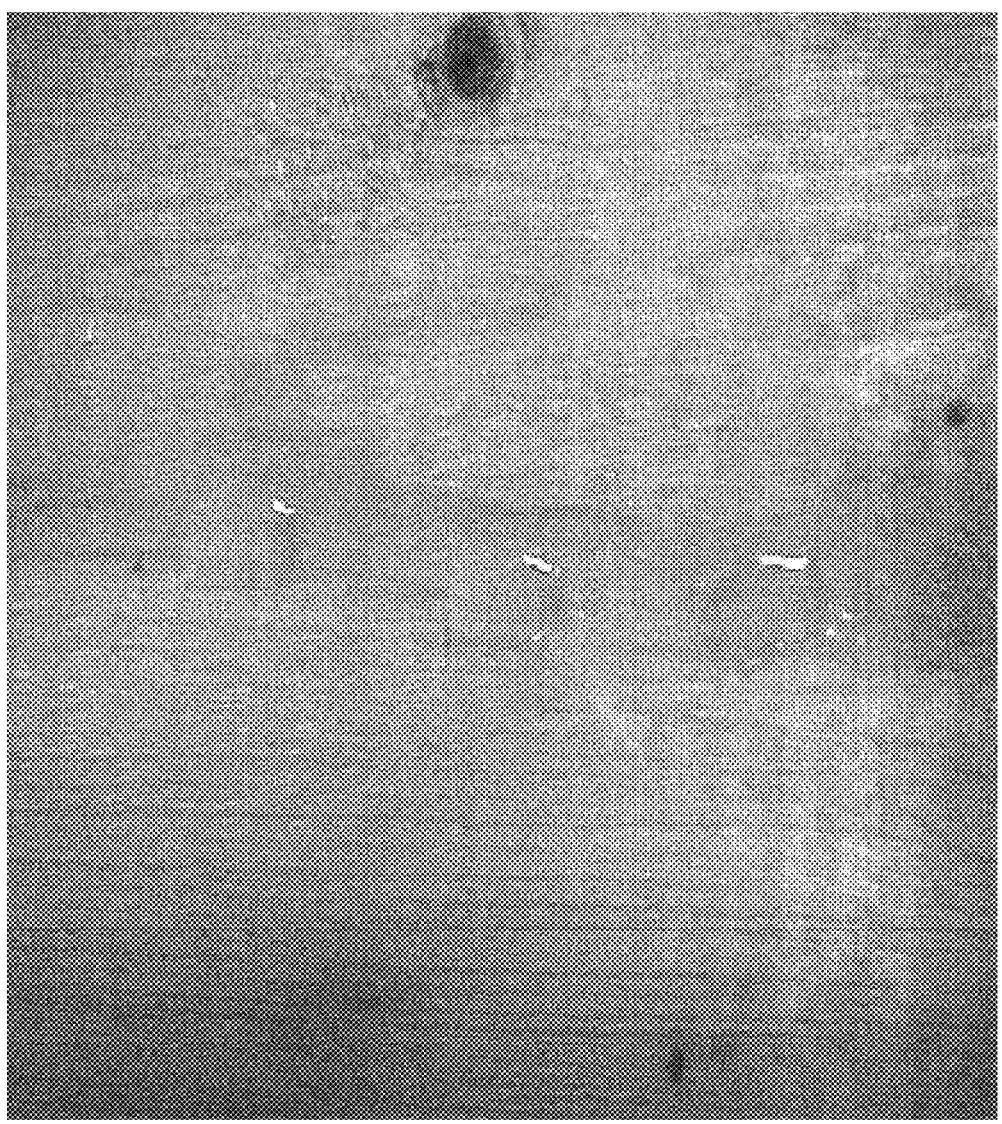
FIG. 1 is a photograph of a wood sample treated with THOMPSON'S Clear Wood Protector and an anti-fungal agent, illustrating the absorption of water into the wood sample one week after treatment.

By "surface" and "surface protecting", as used herein, is meant to broadly capture all parts of a substrate which are exposed to environmental conditions, and are capable of contact with water or moisture in the environment. This includes areas of a porous substrate, into which water or moisture from the environment may penetrate upon exposure.

By "coating" as used herein is meant a polymeric continuous film, which is formed on the surface, as defined above.

The present invention is directed to a formulation containing an aqueous polymer composition comprising a copolymer and water. The copolymer is synthesized from at least one hydrophilic monomer, and at least one hydrophobic ethylenically unsaturated monomer. Examples of monomers useful in the formation of the polymer, and processes for polymer formation are described in U.S. patent application Ser. No. 09/690,387, incorporated herein by reference.

The hydrophilic monomer can be cationic (or acid neutalizable), anionic (or base neutraliizable), or amphoteric, or may be a combination thereof. Both anionic and cationic monomers may be in the same polymer.

Preferably the hydrophilic monomer is a base-neutralizable monomer and is selected from one or more carboxylic, dicarboxylic, sulfonic, and phosphonic acids, or mixtures thereof. Examples of said monomers useful in the present invention include, but are not limited to acrylic acid, methacrylic acid, maleic anhydride, itaconic acid, crotonic acid, styrene sulfonic acid, 2-acrylamido-2-methylpropane sulfonic acid, vinyl sulfonic acid, ethacrylic acid, alpha-chloro-acrylic acid, alpha-cyano acrylic acid, beta methyl-acrylic acid (crotonic acid), alpha-phenyl acrylic acid, sorbic acid, alpha-chloro sorbic acid, angelic acid, cinnamic acid, p-chloro cinnamic acid, beta-styryl acrylic acid (1-carboxy-4-phenyl butadiene-1,3), itaconic acid, maleic acid, citraconic acid, mesaconic acid, glutaconic acid, aconitic acid, fumaric acid, tricarboxy ethylene, 2-acryloxypropionic acid, vinyl sulfonic acid, phosphoric acid, vinyl phosphonic acid, methallyl sulfonic acid, sulfonated styrene, and allyloxybenzenesulfonic acid. Preferably the hydrophilic based-neutralizable monomer is acrylic acid or methacrylic acid.

Another preferred hydrophilic monomer is an acid-neutralizable monomer selected from amine containing monomers such as N,N dialkylaminoalkyl(meth)acrylate, N,N dialkylminoalkylacrylate, dialkylaminoalkyl(meth)acrylamide and N,N dialkylminoalkylacrylamide, where the alkyl groups are independently $C_{1-18}$. Aromatic amine containing monomers such as vinyl pyridine may also be used. Furthermore, monomers such as vinyl formamide, vinylacetamide etc which generate amine moieties on hydrolysis may also be used. Preferably the hydrophilic acid-neutralizable monomer is N,N-dimethylaminoethyl methacrylate, and N,N-dimethylaminopropyl methacrylamide.

Cationic monomers that may be used are the quarternized derivatives of the above monomers as well as diallyldimethylammonium chloride, methacrylamidopropyl trimethylammonium chloride and others.

The base neutralizable monomer and the acid neutralizable monomer may be used together in the same polymer.

The hydrophilic monomer is preferably present in the aqueous polymer composition at from 5 to 50 percent by weight, and preferably from 5 to 25 percent by weight, based on the weight of the polymer.

The hydrophobic monomer can be any ethylenically unsaturated monomer known in the art, or a mixture thereof. Examples of such monomers include, but are not limited to: (meth)acrylates, maleates, (meth)acrylamides, vinyl esters, itaconates, styrenics, unsaturated hydrocarbons and acrylonitrile, nitrogen functional monomers, vinyl esters, alcohol functional monomers, unsaturated hydrocarbons, and (meth)acrylates. Preferred hydrophobic monomers are vinyl monomers and acrylate monomers such as methyl methacrylate, butyl acrylate.

The process for the producing the copolymer is described in U.S. patent application Ser. No. 09/690,387, incorporated herein by reference. The process involves polymerizing at least one hydrophilic monomer and at least one hydrophobic etheylenically unsaturated monomer in a non-aqueous solvent; forming an aqueous polymer dispersion from said non-aqueous polymer solution; and adding an aqueous base or acid. Preferably the base or acid is a volatile base or acid. The addition of the base or acid can occur either before, after, or during the formation of the aqueous polymer dispersion from the non-aqueous polymer solution.

The polymers formed from this type of process are genrally random copolymers. However, other polymer architechtures such as block, star etc may also be used. The special techniques used to synthesize these various types of polymer architechture are well known in the art.

The polymerization of the monomers in a non-aqueous solvent can be done by any means known in the art. The solvent should be miscible with water. Preferably the solvent is capable of forming an azeotrope with water. Examples of solvents useful in the present invention include, but are not limited to, alcohols such as methanol, ethanol, and isopropyl alcohol; glycol ethers; and acetone. If the solvent is a low boiling solvent, such as an alcohol or acetone, it may be stripped from the solution.

Formation of the aqueous polymer dispersion from the non-aqueous polymer solution can occur by several means. First is by the addition of water, or aqueous base or acid, to such an extent that the weight of water in the composition becomes greater that the weight of non-aqueous solvent. Second is by the addition of water or aqueous base or acid, plus a stripping off of the solvent or an azeotrope of the solvent. In whatever means the aqueous polymer solution is formed from the non-aqueous polymer solution, the result is a solution containing at least 50 percent water, based on the total weight of water and non-aqueous solvent.

The final aqueous polymer composition is formed by the combination of the conversion of the polymer solution to an aqueous solution, and the addition of a base or acid. This results in a composition that may be either clear or hazy, depending on the solids content and level of residual solvent. Lower solids levels and higher levels of residual solvent produce clearer solutions.

Bases are used to neutralize the hydrophilic acid monomer and acids are used to neutralize the hydrophilic base monomer. The bases and acids used as neutralization agents can be volatile or non-volatile depending on the application. Mixtures of volatile and non-volatile neutralizing agent may also be used.

Volatile bases useful herein can be evaporated from the solution, or a mixture of said bases. Such bases include, but are not limited to, ammonia, morpholine, the lower alkyl amines, lower alkanol amines, diethananol amine, ethanol amine, 2-dimethylaminoethanol, N-methylmorpholine, and ethylenediamine. Preferred bases include ammonia or ammonium hydroxide, and ethanolamine. Non volatile bases such as NaOH, KOH etc can be used. If the hydrophilic monomer is an acid neutralizable monomer, acids such as hydrochloric acid, nitric acid, sulfuric acid, acetic acid, and other mineral and organic acids may be used. A preferred volatile acid is acetic acid and a preferred non-volatile acid is sulfuric acid.

The base or acid is used in an amount effective to neutralize from 20–100 percent of the neutralizable groups on the polymer. Preferably the base or acid is present in an amount effective to neutralize from 50 to 100 percent of the -neutralizable groups on the polymer.

The aqueous polymer composition of the invention is a solution or dispersion having essentially no stabilizing surfactants, as opposed to a latex or emulsion polymer composition. The advantage of having an aqueous polymer composition is ease of handling and ease of formulating the polymers in to various applications. Several of these applications are illustrated below, and include liquid cleaning solutions and metal and wood protective formulations.

A polymer film formed from the polymer composition according to the invention contains essentially no crosslinking. Crosslinking, as used herein, refers to a chemical crosslink. The absence of crosslinking is confirmed since the polymer films, though insoluble in water, dissolve in the solvent in which the polymer was originally formed. Dissolution of the film in the original solvent means that at least 80 percent of the film dissolved in refluxing solvent within 2 hours.

The film solubility/insolubility can be controlled by the ratio of the hydrophilic to hydrophobic monomer in the polymer, the degree of neutralization and the ratio of volatile to non-volatile neutralization agent used. The desirability of the solubility/insolubility of the film depends on the end use application. In case of metal and wood protection in outdoor applications a completely insoluble film is preferred. However, in a shower spray type of application, it is advantageous for the film to act as a sacrificial layer and be removed over several rinses, keeping the original surface free of dirt. This is an example of an application in which complete insolubility of the polymer film is not required and may indeed be detrimental to performance.

The thickness of the film also depends on the end use application. In the case of metal and wood protection in outdoor applications, the thicker the film (millimeter thickness) the better the properties. However, in some cases, such as the detergent application, the polymer is used in such small amounts (parts per million level) in the aqueous wash bath, that any film if formed would be on a microscopic level (nanometer thickness). Nevertheless, the polymer is still effective as evidenced by the excellent color protection and anti-pilling properties illustrated in the examples.

The polymer composition of the present invention may be used as an ingredient in many types of formulations to provide surface protection. The polymer composition is added into a formulation in any manner known in the applicable art. Formulations having the aqueous polymer composition contain from 0.00001 to 50 percent by weight, preferably from 0.01 to 40 percent by weight of the aqueous polymer composition, based on the weight of the formulation, and most preferably from 0.1 to 20 percent by weight of the polymer composition on a solids/solids basis. The composition may also contain adjutants typically found in formulations, depending on the end use. Such adjutants include, but are not limited to fillers, anti-fungal and anti-microbial agents, pigments, perfumes, surfactants, builders, co-builders, anti-oxidants, enzymes, brighteners, dispersants, anti-foaming agents, preservatives, water-softening agents, sunscreen agents, and mixtures thereof. One advantage of this technology is the ease of handling and formulation of the polymer composition into many types of formulations used to protect the surfaces of a wide variety of substrates.

The polymer composition can be synthesized in a manner to include hydrophilic acid or base neutralizable monomers. Films formed on substrates from such a polymer may be removed using an alkaline cleaning solution or acid cleaning solution respectively. The ease of removal of these films would depend on the factors discussed earlier such as ratio of the hydrophilic to hydrophobic monomer in the polymer, the degree of neutralization and the ratio of volatile to non-volatile neutralization agent used.

The formulations of the present invention may be applied to a substrate to form a thin film. Said film provides a hydrophobic barrier on the substrate to provide surface protection. The formulation may be applied to a substrate by any means known in the art, including but not limited to, spray, immersion, brushing, or flow-through. Substrates benefiting from treatment with the composition of the invention include, but are not limited to, wood, metal, glass, ceramics, leather, concrete, fabric, textiles, plastics, vinyl, rock, skin, hair, carpet, paper, cardboard, upholstery, non-wovens, and other substrates exposed to the environment.

Formulations, made with the polymer composition have an almost endless range of uses. Examples of these uses are listed below for illustrative purposes. One of skill in the art will recognize many other applications in which the surface protection obtained from formulations of this invention may be beneficial.

The polymer composition may be used as a coating to protect a variety of finishes such as automobiles, paint on the outside of building, roof tiles, and as coatings on a variety of materials that need to resist the environment.

Typically oily films are applied to metallic parts to prevent corrosion during transport. The metallic parts are then cleaned with solvents to remove the oily finish before they are painted. The polymers of this invention overcome this environmentally unfriendly process because, they can be delivered from an aqueous solution, can then be removed by an aqueous solution if needed. However, they need not be removed and can be directly painted over saving time money and the environment. Moreover, by adjusting the glass transition temperature of the polymer the film can be designed to be stiff or flexible and therefore can adhere to a variety of metal surfaces such as stainless steel, mild steel, copper brass tin aluminum, cast iron etc.

Formulations made with the polymer composition of this invention are useful in metal working fluids. The polymer can be incorporated into these formulations and provide a protective film to the newly cut surface while the metal is being cut.

While formulations of the present invention are very useful in a variety of coating applications, their usefulness extends beyond conventional coatings. These include end-uses such as providing anti-pilling properties, and as a color protection agent in detergents and fabric softeners. In textile finishing applications the polymers may be applied in the finishing step along with cationic softeners to minimize abrasion and loss of dyes during subsequent laundering, and wear and tear during use. The polymer composition is also useful in preventing backstaining of denim during the stone-washing process.

In some applications, such as in a car wash, the polymer composition can be adjusted to provide a protective coating to the car surface, yet dissolve in the next wash removing built-up dirt.

The polymer composition of the present invention can be formulated and applied to a fabric as a fabric finish during the textile processing application. Fabric thus coated is found to exhibit anti-pilling properties. Fabrics treated with the coating composition also resist fading and this treatment can last several washes.

The polymer composition is useful as a dispersant, which can be used in many formulations, such as those used to treat textiles. The materials dispersed may be dyes, pigments, clays, dirt, soils and other hard to disperse moeities.

The polymer composition of this invention can be added to detergent and fabric softener formulations. These polymers are then introduced in to the laundering process during the wash and or rinse cycle, and provide color protection and pill reduction properties to fabrics thus treated. Furthermore, they may be used to deliver actives such as perfumes and enzymes from a detergent during the wash cycle, and then release these ingredients during the rinse cycle where they are more effective. They can be used in autodish formulations to minimize filming and spotting and deliver rinse aids into the rinse cycle. These are just a few of the examples where the polymer composition the present invention is useful in controlled-release formulations.

The base neutralizable polymers of this invention are soluble at high pH and insoluble at low pH. The acid neutralizable polymers show opposite solubility behavior. Hence, these polymers can be used as pH triggered control release agents in aqueous systems.

The polymer compositions may used to protect surfaces in hard surface cleaning formulations, where they can act as a protective film. The polymer film may then be removed during the cleaning process.

The polymer compositions of the present invention may also be used a water barriers in paper and board coating applications.

The polymer compositions may be used to disperse hydrophobic materials such as clays, perfumes, etc. into aqueous systems. They may be used in mining applications to disperse ores.

The acid neutralizable polymers of this invention are particularly suited for protective floor finishes. Typical polymeric finishes are crosslinked by heavy metals, which are toxic. These finishes have to be removed by solvents which generates another source of hazardous waste. The acid neutralizable polymers of this invention can be used to form a protection floor finish from an aqueous medium. The finish will be resistant to normal wear and tear as well as normal alkaline cleaners. However, once a year the finish can be removed by an acidic cleaner (no harsh solvents) and can then be reapplied.

In oilfield applications, the polymer compositions may be pumped in to a rock formation that produces water (heavy brines). The pH of the treatment formulation may be then altered, precipitating the polymer out of solution. The polymer precipitate then plugs up the pores of the water bearing formation. This minimizes the amount of water produced and maximizes the amount of oil produced.

The polymers of this invention may also be used in personal care applications. A specific application that base neutralizable polymers of this invention are extremely suited to are sun screen formulations with UV protection. The polymers of this invention will form a water-resistant film on the skin and prevent the UV protection agents from being washed off. However, the polymeric film may be removed by the alkaline cleaning agents in bar soaps when the person showers.

The polymer composition may also be used in water treatment applications to minimize corrosion.

The polymer composition of the invention may also be used in agricultural applications to coat actives like fertilizers and seeds. The coated actives can be introduced into the soil and the actives released over a period of time. The time period of release can be controlled by the pH range of the soil, the ratio of hydrophobe to hydrophilic monomer in the polymer, the amount of neutralization and the ratio of volatile to non-volatile neutralization agent.

The polymer composition may also be used to prolong the effect of insect repellants and biocide/anti-microbials in spray applications.

The polymer composition is also useful in protecting non-woven materials, and especially cationic polymer compositions.

The following examples are presented to further illustrate and explain the present invention and should not be taken as limiting in any regard.

SYNTHESIS OF THE AQUEOUS POLYMER COMPOSITION

EXAMPLE 1

139.8 grams isopropanol were added to a 2-L four-neck flask equipped with a condenser, thermometer, and stainless steel paddle agitator. The solution was stirred and purged with a gentle stream of nitrogen for 15 minutes. After the purge ended, the solution was heated to reflux and once a steady reflux was obtained 66.0 grams methyl methacrylate, 20.0 grams butyl acrylate, and 14.0 grams acrylic acid were added over 2.0 hours via monomer pump. Simultaneously 8.0 grams of isopropanol and 2.0 grams Vazo 67 were added over 2.5 hours via syringe pump. The reaction was maintained at reflux temperature and the contents were held at reflux for 15 minutes after the initiator slow-addition finished. The flask was then equipped with a Dean-Stark trap and approximately 100.0 grams isopropanol was stripped off. The contents were then cooled to 60° C. and a solution of 140.0 grams deionized water and 11.5 grams of a 29.5% ammonium hydroxide solution were added with good agitation. The polymer dissolved readily, and the contents were heated to reflux and the remaining isopropanol was removed. The solution was cooled to 30° C. and the viscosity was adjusted with water if necessary. The resulting solution polymer was 24.5% solids with a pH of 7.1 and had a viscosity of 430 cPs. The polymer, once dried was insoluble in caustic and boiling water.

EXAMPLE 2

Cationic Polymer

The polymerization was conducted in the same manner as Example 1, except that 85.0 grams methyl methacrylate, and 15.0 grams dimethylaminopropyl methacrylate were used as the monomers. The polymer was neutralized with acetic acid and dispersed in water. The resulting solution polymer was 25.7% solids with a pH of 6.0. The polymer, once dried was insoluble in boiling water.

EXAMPLE 3

Amphoteric Polymer

The polymerization was conducted in the same manner as Example 1 except that 50.0 grams butyl acrylate, 30.0 grams methyl methacrylate, 10.0 grams acrylic acid, and 10.0 grams dimethylaminopropyl methacrylamide were used as the monomers. The polymer was neutralized with ammonia and dispersed in water. The resulting solution polymer was 17.6% solids with a pH of 8.4. The polymer, once dried was insoluble in boiling water.

EXAMPLE 4

Anionic Polymer

The polymerization was conducted in the same manner as Example 1 except that 20.0 grams methyl methacrylate, 60.0 grams butyl acrylate, and 20.0 grams methacrylic acid were used as the monomers. The neutralization agent was 30 grams of a 28% solution of ammonium hydroxide. The resulting solution polymer was 22.5% solids with a pH of 9.5 and a viscosity of 805 cPs. The polymer, once dried was insoluble in caustic and boiling water.

EXAMPLE 5

The polymerization was conducted in the same manner as Example 4 except that 50.0 grams methyl methacrylate, 40.0 grams butyl acrylate, and 10.0 grams acrylic acid were used as the monomers. The resulting solution polymer was 20.0% solids with a pH of 10.2 and a viscosity of 3250 cPs. The polymer, once dried was insoluble in caustic and boiling water.

EXAMPLE 6

Cationic Polymer

The polymerization was conducted in the same manner as Example 1, except that 70 grams methyl Styrene, and 30.0 grams dimethylaminoethyl methacrylate were used as the monomers. The polymer was neutralized with acetic acid and dispersed in water.

EXAMPLE 7

Cationic Polymer

The polymerization was conducted in the same manner as Example 1, except that 80.0 grams methyl Styrene, and 20.0 grams dimethylaminoethyl methacrylate were used as the monomers. The polymer was neutralized with acetic acid and dispersed in water.

EXAMPLE 8

Cationic Polymer

The polymerization was conducted in the same manner as Example 1, except that 40 grams of butyl acrylate, 40 grams of methylmethacrylate and 20 grams of methacrylamidopropyl trimethylammonium chloride (MAPTAC) were used as the monomers.

EXAMPLE 9

Anionic Polymer with Non-Volatile Base

The polymerization was conducted in the same manner as Example 1, except that 90.0 grams methyl Styrene, and 10.0 grams acrylic acid were used as the monomers. The polymer was neutralized with sodium hydroxide and dispersed in water.

EXAMPLE 10

Metal Protection

Mild steel coupons were cleaned with xylene and then dried them with acetone. Directly following this cleaning step, solutions of the polymer compositions of Examples 3 and 4 at 3% were sprayed onto the coupons, and the coupons were dried overnight. The next day the coupons were place in a tap water bath at room temperature and allowed to soak for several hours. The coupon treated with the polymer of Example 4 was far less corroded than a control coupon and the coupon treated with the polymer of Example 3 was less corroded than the control coupon.

EXAMPLE 11

Upholstery Protection

1% solutions of Example 2 were applied to a heavy cotton duck (an often used upholstery fabric) and allowed these swatches to dry overnight. The following day, a droplet of water was placed on each swatch and the time it took for the swatch to absorb the droplet was recorded. The polymer of Example 2 prevented the water from being absorbed for 6 minutes and 32 seconds. A water droplet placed onto untreated heavy cotton duck is absorbed in 4 seconds.

EXAMPLE 12

Wood Protection

Figure 2:
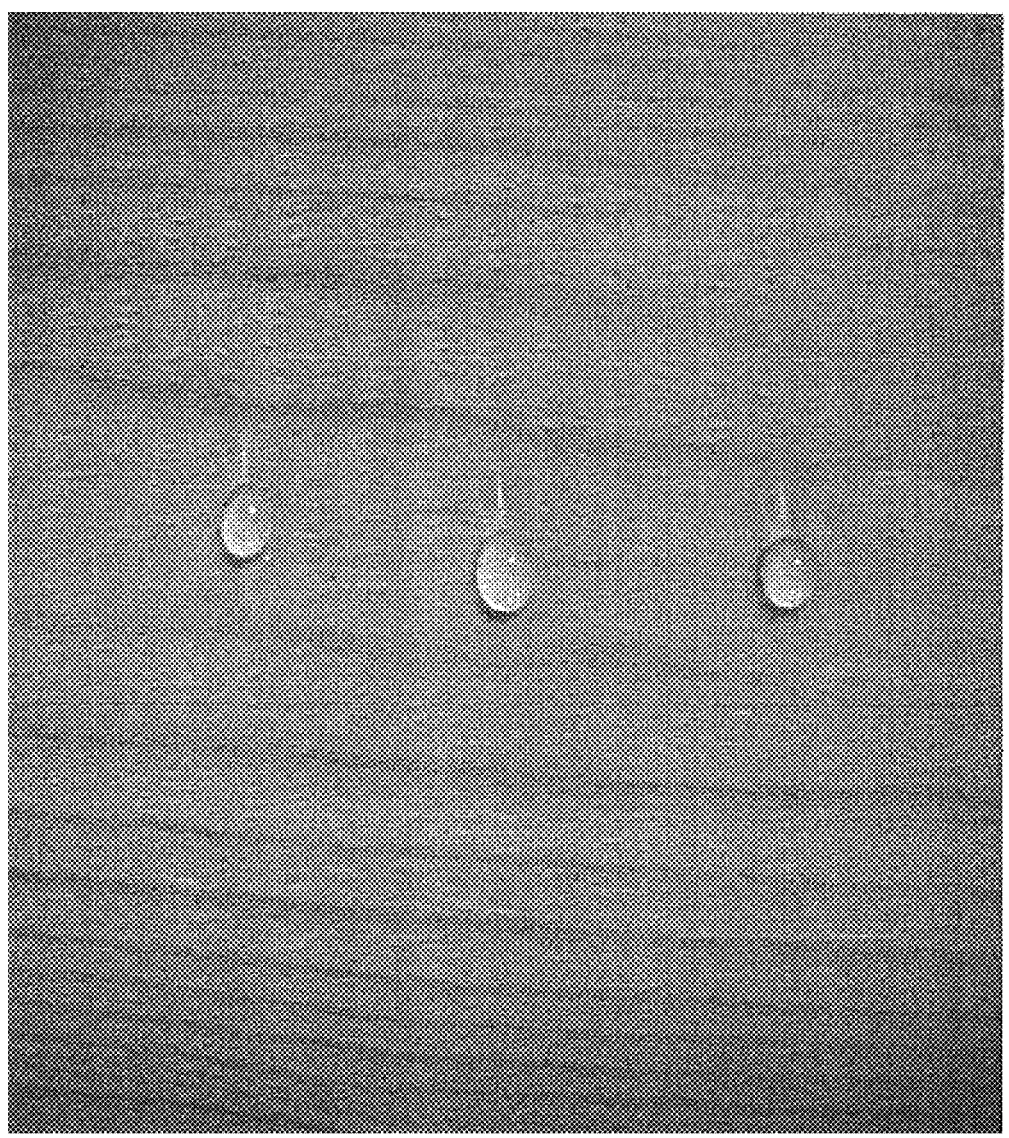
FIG. 2 is a photograph of a wood sample treated with the polymer composition of Example 4 and an anti-fungal agent, illustrating the prevention of absorption of water into the wood sample one week after treatment.

An anti-fungal agent, M-1 Additive made by the JOMAPS Company in Alpharetta Ga., was added to the polymer composition of Example 4 and also to THOMPSON's Clear Wood Protector at dosage on package (2.2% on solution). Wood samples were coated with these samples and placed outside to weather with a blank untreated sample. These samples were treated with droplets of water after a week. The water on the Thompson's wicked in to the wood (FIG. 1). The water on the Example 4 treated sample beaded and was not absorbed in to the wood (FIG. 2).

EXAMPLE 13

Detergent Application

The polymers of this invention were evaluated in a detergent application using a full scale washing machine for color protection and anti-pilling properties. 118 g/Load XTRA liquid detergent (USA Detergents) containing 1 wt % polymer was used in the test. The test used Chattanooga City, Tenn. $H_2O$ (typically 70 ppm hardness), with a 10 minute wash and 3 minute rinse and a wash temperature of 93° F. 3 black knit & 3 red knit swatches attached to one pillowcase and 8 extra cases added as ballast. The test was conducted over 5 complete cycles (wash/dry). The swatches were evaluated visually (Table 1) and then with the spectrophotometer (Table 2).

TABLE 1

| Polymer Number | Polymer Composition | Pilling performance | Color loss |
| --- | --- | --- | --- |
| Control | — | Much pilling | Faded to brown |
| Example 4 | 60 BA/20 MMa/20 MAA 100% Neutralized | Slight pilling | Moderate fading |
| Example 2 | 85 MMA/DMAPMA 15 neutralized with acetic acid | Very Slight pilling | No fading |
| Example 3 | 50 BA/30 MMA/10 DMAPMA/10 AA Neutralized with ammonia | Slight pilling | Moderate fading |

TABLE 2

| | | Delta E* (compared to new swatch) | |
| --- | --- | --- | --- |
| Sample | Sample description | Red | Black |
| Control (no polymer) | — | 4.01 | 6.67 |
| Example 6 | Styrene - DMAEMA (30 wt %) | 3.22 | 3.63 |
| Example 7 | Styrene - DMAEMA (20 wt %) | 3.49 | 3.38 |
| Example 2 | MMA - DMAPMA (15 wt %) | 3.32 | 3.14 |
| Example 8 | BA/MMA/MAPTAC 40/40/20 | 4.63 | 7.26 |
| Example 9 | MMA/AA 90/10 NaOH neutralized | 4.11 | 6.65 |
| Example 4 | BA/MMA/MAA 60/20/20 wt % | 2.84 | 6.82 |

The data in the Tables above indicate that the polymers of the invention reduce pilling and minimize color loss (lower Delta E values) as compared to a control.

EXAMPLE 14

Granular Detergent Test Composition Preparation

Typical heavy duty granular detergent compositions can be prepared containing one or more hydroxy compounds of this invention. These granular detergent compositions all have the following basic formula:

TABLE 3

| Component | Wt. % |
|---|---|
| $C_{12}$ Linear alkyl benzene sulfonate | 9.31 |
| $C_{14-15}$ alkyl ether (0.35 EO) sulfate | 12.74 |
| Zeolite Builder | 27.79 |
| Sodium Carbonate | 27.31 |
| PEG 4000 | 1.60 |
| Dispersant | 2.26 |
| $C_{12-13}$ Alcohol Ethoxylate (9 EO) | 1.5 |
| Sodium Perborate | 1.03 |
| Enzymes | 0.59 |
| Polymer 4 | 3.0 |
| Perfume, Brightener, Suds Suppressor, Other Minors, Moisture, Sulfate | Balance |
| | 100% |

EXAMPLE 15

Liquid Detergent Test Composition Preparation

Typical heavy duty liquid detergent compositions can be prepared containing one or more hydroxy compounds of this invention. These granular detergent compositions all have the following basic formula:

TABLE 4

| Component | Wt. % |
|---|---|
| C12–15 alkyl ether (2.5) sulfate | 38 |
| C12 glucose amide | 6.86 |
| Citric Acid | 4.75 |
| C12–14 Fatty Acid | 2.00 |
| Enzymes | 1.02 |
| MEA | 1.0 |
| Propanediol | 0.36 |
| Borax | 6.58 |
| Dispersant | 1.48 |
| Na Toluene Sulfonate | 6.25 |
| Polymer 2 | 1.0 |
| Dye, Perfume, Brighteners, Preservatives, Suds Suppressor, Other Minors, Water | Balance |
| | 100% |

EXAMPLE 16

Granular Detergent Test Composition Preparation

Typical granular detergent compositions can be prepared containing one or more hydroxy compounds of this invention. These granular detergent compositions all have the following basic formula:

TABLE 5

| Component | Example Wt. % | Comparative Wt. % |
|---|---|---|
| Na $C_{12}$ Linear alkyl benzene sulfonate | 9.40 | 9.40 |
| Na $C_{14-15}$ alkyl sulfonate | 11.26 | 11.26 |
| Zeolite Builder | 27.79 | 27.29 |
| Sodium Carbonate | 27.31 | 27.31 |
| PEG 4000 | 1.60 | 1.60 |
| Dispersant, Na polyacrylate | 2.26 | 2.26 |
| $C_{12-13}$ alkyl ethoxylate (E9) | 1.5 | 1.5 |
| Sodium Perborate | 1.03 | 1.03 |
| Polymer 3 | 2.0 | 0 |
| Other Adjunct ingredients | Balance | Balance |
| | 100% | 100% |

EXAMPLE 17

Typical dilute fabric softener formulations are listed below.

TABLE 6

Formulations of Dilute Traditional Softeners (Single Active)[a]

| Ingredient | (%) |
|---|---|
| Formula A | |
| distearyldimetylammonium Chloride (75% active) | 6–9 |
| Polymer of Example 2 | 0.1–3.0 |
| Perfume | 0.2–0.5 |
| Colorant | 0.001 |
| Water | Balance |
| Formula B | |
| Quaternary dialkylimidazolines (75% active) | 6–9 |
| Polymer of Example 7 | 0.1–3.0 |
| Perfume | 0.2–0.5 |
| Colorant | .0001 |
| Preservative | + |

EXAMPLE 18

Examples of Concentrated Fabric Softener Compositions

TABLE 7

Ready-to-Use Rinse Conditioners at Triple Concentration (Mixed Actives)

| Ingredient | (%) |
|---|---|
| Formula C | |
| distearyldimethylammonium chloride 75% | 14 |
| Polymer of Example 8 | 3 |
| Lanolin | 2 |
| Ethoxylated fatty acid | 4 |
| $CaCl_2$ | 0.05 |
| Water, perfume, color | Balance |
| Formulation D | |
| distearyldimethylammonium chloride | 5–10 |
| Amidoamine | 5–10 |
| Imidazoline | 3.75–5.25 |
| Polymer of Example 2 | 0.1–2.0 |
| Electrolyte | 0.05–.4 |
| Water, perfume, color | Balance |

EXAMPLE 19

Oil Field Use

Acetic Acid was added dropwise to 20% solution of the polymer of Example 4. Large white clumps of polymer were formed. A dilute solution of the polymer of Example 4 can be pumped in to the water producing zones of an oil well. The pH of the solution can then be lowered by addition of ester such as ethylacetate which will hydrolyze to produce acetic acid. The polymer will precipitate out and plug the pores of the zone thus reducing or minimizing the production of water and increasing the production of oil.

EXAMPLE 20

Textile Application

The polymer of Example 7 was padded on to cotton fabric during the textile finishing process. The weight of the polymer put on to the fabric was 1 weight percent by weight of the fabric. The treated and finished fabric was then run through 25 cycles of a regular washing machine. The treated fabric exhibited less dye loss and wear and tear as compared to an untreated fabric.

EXAMPLE 21

Textile Application

The polymer of Example 2 was included in a process of stone washing of denim fabrics. The process involves removal of indigo dye from denim using pumice stones (for mechanical action) and cellulase enzymes (chemical action). The stone washed denim using polymer 2 had significantly less redeposition of the indigo (usually called backstaining) than a control which did not contain the polymer.

EXAMPLE 22

Typical Hard Surface Cleaning Formulations

| Ingredient | wt % |
|---|---|
| Acid Cleaner | |
| Citric acid (50% solution) | 12.0 |
| C12–15 linear alcohol ethoxylate with 3 moles of EO | 5.0 |
| Alkylbenzene sulfonic acid | 3.0 |
| Polymer of Example 2 | 1.0 |
| Water | 79.0 |
| Alkaline Cleaner | |
| Water | 89.0 |
| Sodium tripolyphosphate | 2.0 |
| Sodium silicate | 1.9 |
| NaOH (50%) | 0.1 |
| Dipropylene glycol monomethyl ether | 5.0 |
| Octyl polyethoxyethanol, 12–13 moles EO | 1.0 |
| Polymer of example 4 | 1.0 |

EXAMPLE 23

Typical Automatic Dishwash Formulation

| Ingredients | Amounts |
|---|---|
| Sodium tripolyphosphate | 25.0 |
| Sodium carbonate | 25.0 |
| C12–15 linear alcohol ethoxylate with 7 moles of EO | 3.0 |
| Polymer of Example 4 | 4.0 |
| Sodium sulfate | rest |

EXAMPLE 24

Car Wash Rinse Off Aid Formulation

| Ingredients | wt % |
|---|---|
| Water | 80 |
| Butyldiglycol | 10 |
| Polymer of Example 2 | 10 |

EXAMPLE 25

Deposition of Fragrances During Wash Cycles

A fruity masking fragrance (0.5%) was emusified in water using the polymer of Example 2 and 4 using a high shear mixer. This emulsified fragrance was then run through a typical wash cycle using 1.0 g/liter of Arm and Hammer Free (free of fragrances) and 0.5% fragrance. The washed swatches were then evaluated by a panel. The results of the panel are listed in the Table 8.

TABLE 8

| Polymer | Average results of the Panel |
|---|---|
| Control | — |
| Polymer 2 | Significantly more fragrant than the control |
| Polymer 4 | Slightly more fragrant than the control |

EXAMPLE 26

Protection of Exterior Paint

Two identical freshly painted wood panel were sprayed with a 5% aqueous solution of Example 2 and 4. These panels along with a control panel were then subjected to an outdoor aging test for a period of 6 months. The panels treated with polymers of example 2 and 4 exhibited less wear and tear than the control.

EXAMPLE 27

Personal Care Formulation

| Ingredients | Wt % |
|---|---|
| Glycerin | 5.0 |
| Polymer of Example 4 | 2.0 |
| PEG 100 stearate | 5.0 |
| Isostearyl stearate | 4.0 |
| Octyl methoxycinnamate | 7.5 |
| Butyl methoxydibenzoyl-methane | 1.5 |
| Hexyl methicone | 5.0 |
| DI water | rest |

EXAMPLE 28

Control Release

A 20% aqueous solution of the polymer of Example 2 was taken in a beaker equipped with a stir bar. The pH of this solution was 6.0 and the solution was clear. A few drops of 10% sodium hydroxide solution was added with stirring to raise the pH of the solution. The solution became hazy around pH 8.5 and was completely opaque at pH 11 indicating loss in solubility of the polymer at the higher pH. Thus these types of polymers can be used to release actives in a controlled manner. For example, an active such as a protease enzyme may be encapsulated and protected in the wash cycle (higher pH) but the polymer would dissolve to release it in the rinse (lower pH).

What is claimed is:

1. An aqueous polymer composition comprising:
    a copolymer having at least one hydrophilic and at least one hydrophobic ethylenically unsaturated monomer; and
    water;
    wherein said aqueous polymer composition is a solution or a dispersion having substantially no stabilizing surfactants, and wherein a film formed from said aqueous polymer composition comprises substantially no crosslinking.

2. The composition of claim 1 wherein said hydrophilic monomer is a cationic, anionic, or amphoteric monomer.

3. The composition of claim 1 wherein said film formed from said polymer composition is insoluble in water.

4. The composition of claim 1 wherein said aqueous polymer composition is clear.

5. A surface-protecting formulation comprising:
the polymer composition of claim 1; and
a component selected from the group consisting of fillers, anti-fungal and anti-microbial agents, pigments, perfumes, surfactants, builders, co-builders, anti-oxidants, enzymes, brighteners, dispersants, anti-foaming agents, preservatives, water-softening agents, sunscreen agents and mixtures thereof.

6. The composition of claim 5 wherein said film formed from said polymer composition is insoluble in water.

7. The formulation of claim 5 comprising no volatile base.

8. The formulation of claim 5 further comprising sodium hydroxide.

9. The formulation of claim 5 wherein said copolymer further comprises an acid functionality.

10. The formulation of claim 5 wherein said film formed from said copolymer composition is removable using an acid or alkaline cleaning solution.

11. The formulation of claim 5 wherein said copolymer further comprises a star polymer.

12. The formulation of claim 5 wherein said aqueous polymer composition is clear.

13. The formulation of claim 5 wherein said hydrophilic monomer is cationic, anionic or amphoteric.

14. The formulation of claim 5 comprising from 0.00001 to 40 percent by weight of said aqueous polymer composition, based on the surface-protecting formulation.

15. The formulation of claim 5 comprising 0.1 to 20 percent by weight of said copolymer n a solids/solids basis.

16. A process for imparting water resistance to a substrate comprising applying to a substrate the surface-protecting formulation of claim 5.

17. A coated substrate comprising:
a substrate;
a film on at least one surface of said substrate formed from the aqueous polymer composition of claim.

18. The coated substrate of claim 17 wherein said film is applied to said substrate by spray, brushing, immersion, or flow-through.

19. One or more computer readable media as recited in claim 18, wherein the indexing structure contains a root and zero or more intervening nodes between the root and the leaf nodes, further comprising computer-executable instructions that, when executed, direct a computing device to authenticity of the root and any intervening nodes on a path from the root to the leaf node associated with the target encrypted block.

20. The process comprising the use of the polymer of claim 1 in an application selected from the group consisting of fabric cleaning, hard surface cleaning, fabric softening, autodish washing, control release, textile processing, oilfield processing, water treatment, metal working, personal care product formulating, fabric protection, and paint formulation.

* * * * *

UNITED STATES PATENT AND TRADEMARK OFFICE
CERTIFICATE OF CORRECTION

PATENT NO. : 7,063,895 B2
APPLICATION NO. : 09/920498
DATED : June 20, 2006
INVENTOR(S) : Klein Rodrigues et al.

It is certified that error appears in the above-identified patent and that said Letters Patent is hereby corrected as shown below:

Please delete claim 19 in its entirety and replace it with the following claim 19 -

--19. The coated substrate of claim 17 wherein said substrate is selected from the group consisting of wood, metal, glass, ceramics, leather, concrete, fabric, textiles, plastics, vinyl, carpet, paper, upholstery, rock, hair and skin.--

Signed and Sealed this

Nineteenth Day of December, 2006

JON W. DUDAS
*Director of the United States Patent and Trademark Office*